(12) United States Patent
Watanabe et al.

(10) Patent No.: US 9,198,577 B2
(45) Date of Patent: Dec. 1, 2015

(54) DISPLAY PROCESSING METHOD AND APPARATUS

(71) Applicants: FUJITSU LIMITED, Kawasaki-shi, Kanagawa (JP); The University of Tokyo, Tokyo (JP)

(72) Inventors: Masahiro Watanabe, Kawasaki (JP); Satoshi Fuchikami, Fukuoka (JP); Yoshimasa Kadooka, Kawasaki (JP); Toshiaki Hisada, Tokyo (JP); Seiryo Sugiura, Tokyo (JP); Takumi Washio, Tokyo (JP); Jun-ichi Okada, Tokyo (JP)

(73) Assignees: FUJITSU LIMITED, Kawasaki (JP); THE UNIVERSITY OF TOKYO, Tokyo (JP)

( * ) Notice: Subject to any disclaimer, the term of this patent is extended or adjusted under 35 U.S.C. 154(b) by 139 days.

(21) Appl. No.: 13/940,759

(22) Filed: Jul. 12, 2013

(65) Prior Publication Data

US 2014/0023261 A1    Jan. 23, 2014

(30) Foreign Application Priority Data

Jul. 17, 2012    (JP) .................................. 2012-158754

(51) Int. Cl.
*G06K 9/00* (2006.01)
*A61B 5/00* (2006.01)
*G06T 19/00* (2011.01)

(52) U.S. Cl.
CPC .............. *A61B 5/0033* (2013.01); *G06T 19/00* (2013.01); *G06T 2210/24* (2013.01); *G06T 2210/41* (2013.01)

(58) Field of Classification Search
None
See application file for complete search history.

(56) References Cited

U.S. PATENT DOCUMENTS 8,576,225 B2 * 11/2013 Garg et al. ..................... 345/420
2013/0004049 A1 * 1/2013 Weeden ........................ 382/131

OTHER PUBLICATIONS

"AVS/Express Module reference", Cybernet Systems Co., Ltd., p. T-84, (Aug. 2010).
W. Schroeder et al., "The Visualization Toolkit: An Object-Oriented Approach to 3D Graphics," 2nd edition, Prentice Hall PTR, pp. 200-203, (1998).

* cited by examiner

*Primary Examiner* — Hadi Akhavannik
(74) *Attorney, Agent, or Firm* — Staas & Halsey LLP

(57) ABSTRACT

A disclosed method includes: identifying an axis that is a straight or curved line inside of a space; first generating plural surface regions that are orthogonal to the identified axis; second generating, from a first vector provided at each vertex of an unstructured grid disposed inside of the space, a second vector at each point of plural points on a surface region for each of the generated plural surface regions; and displaying an arrow corresponding to the generated second vector.

6 Claims, 15 Drawing Sheets

DISPLAY PROCESSING METHOD AND APPARATUS

CROSS-REFERENCE TO RELATED APPLICATIONS

This application is based upon and claims the benefit of priority of the prior Japanese Patent Application No. 2012-158754, filed on Jul. 17, 2012, the entire contents of which are incorporated herein by reference.

FIELD

This invention relates to a display processing method and apparatus.

BACKGROUND

Along with the enhancement of the processing ability of the computer, a numerical analysis of a fluid inside of various objects is conducted. For example, the numerical analysis for reproducing a function of a heart is performed with respect to a blood flow inside of the heart.

Conventionally, in such a numerical analysis, the blood flow is displayed using following methods:

(A) Vector Display

Blood flow vectors obtained by the numerical analysis are displayed as arrows as they are.

(B) Particle Flow

Plural particles having no weight are inputted from an arbitrary position in a vector field. Movement direction and amount of each particle are calculated depending on either of the steady-state analysis and non-steady-state analysis. In other words, the particles are moved in sequence to display the flow.

When the blood flow inside of the heart is simply displayed, displays as illustrated in FIGS. 1 and 2 may be conducted. FIGS. 1 and 2 illustrate the blood flows in left and right ventricles in different angles. However, the vectors obtained by the numerical analysis are display as they are, therefore, the states of the blood flows are unclear, because a lot of arrows overlap.

RELATED ARTS

Non-Patent Documents

[Non-Patent Document 1] "AVS Express Module reference", CYBERNET SYSTEMS CO., LTD., p. T-84, August 2010

[Non-Patent Document 2] SCHROEDER WILL et al., "The visualization toolkit", 2nd edition, Prentice Hall PTR, ISBN 0-13-954694-4, pp. 200-203, 1997

SUMMARY

A display processing method relating to one mode of this invention includes: (A) identifying an axis that is a straight or curved line inside of a space; (B) first generating plural surface regions that are orthogonal to the identified axis; (C) second generating, from a first vector provided at each vertex of an unstructured grid disposed inside of the space, a second vector at each point of plural points on a surface region for each of the generated plural surface regions; and (D) displaying an arrow corresponding to the generated second vector.

The object and advantages of the embodiment will be realized and attained by means of the elements and combinations particularly pointed out in the claims.

It is to be understood that both the foregoing general description and the following detailed description are exemplary and explanatory and are not restrictive of the embodiment, as claimed.

DESCRIPTION OF EMBODIMENTS

In this embodiment, as one example, a case is presumed where results of the numerical analysis for the heart are displayed as vectors. However, this embodiment can be applied to a case where the results of the numerical analysis for other objects are displayed as vectors.

Figure 3:
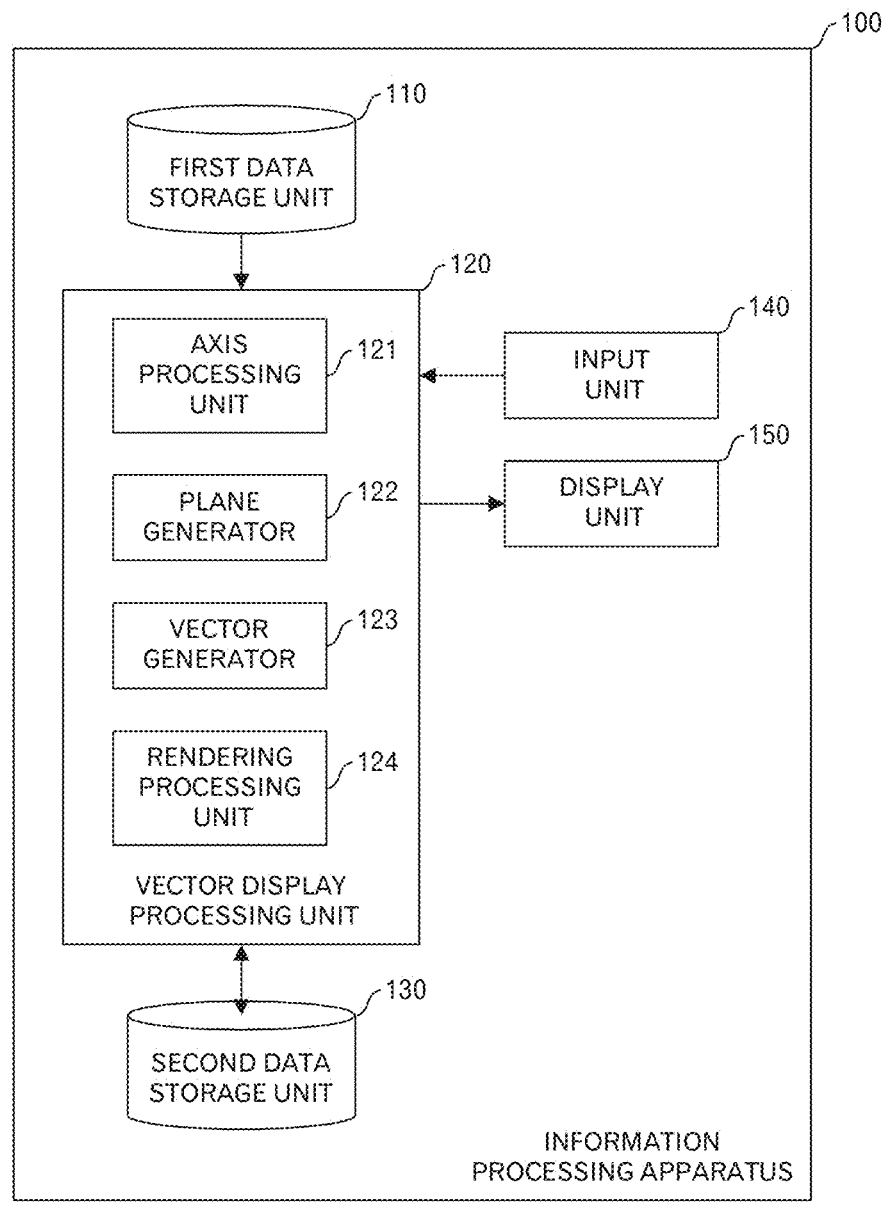
FIG. 3 is a functional block diagram of an information processing apparatus relating to an embodiment of this invention.

FIG. 3 illustrates a configuration of an information processing apparatus 100 relating to this embodiment. The information processing apparatus 100 relating to this embodiment includes a first data storage unit 110, a vector display processing unit 120, a second data storage unit 130, an input unit 140 and a display unit 150. The vector display processing unit 120 includes an axis processing unit 121, a plane generator 122, a vector generator 123 and a rendering processing unit 124.

The first data storage unit 110 stores, as results of the numerical analysis, coordinates of each vertexes of each tetrahedral element, element information (e.g. attributes of the tetrahedral element (e.g. attribute representing whether the tetrahedral element belongs to portions of the heart such as the heart muscle or portion in which the blood flows.)), a physical value at each vertex (e.g. vector representing a velocity of the blood flow in case of the tetrahedral elements included in the portion in which the blood flows), and a physical value in each tetrahedral element. Because the results of the numerical analysis change with respect to time, the results of the numerical analysis includes the results of the numerical analysis for each time step.

The vector display processing unit 120 performs a vector display processing for displaying a vector that is set at each vertex of the tetrahedral element as an arrow.

The axis processing unit 121 in the vector display processing unit 120 performs a processing for identifying an axis to determine a surface region that is used in a following processing in the right ventricle or left ventricle in this embodiment. The plane generator 122 performs a processing for generating plural surface regions that intersect perpendicularly to the axis identified by the axis processing unit 121. The vector generator 123 generates a vector at each point on each surface region of the plural surface regions that are generated by the plane generator 122, from the vectors at each vertex of each tetrahedral element. The second data storage unit 130 stores data such as axis, plane and vector. The rendering processing unit 124 performs a processing for rendering portions of the heart such as heart muscle and arrows each of which represents the vector generated for each surface region, to display the objects onto the display unit 150. The input unit 140 accepts input and selection data from a user.

Figure 4:
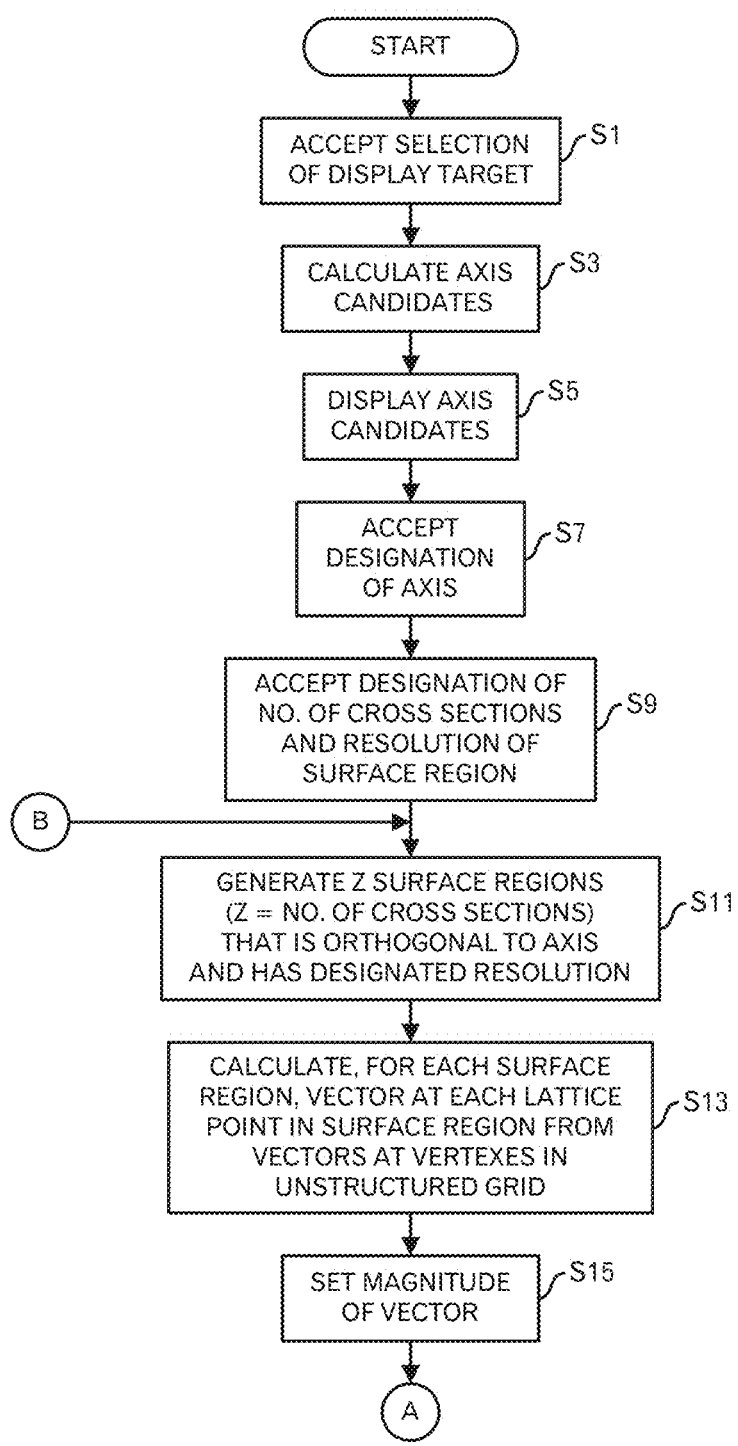
FIG. 4 is a diagram depicting a processing flow relating to this embodiment.

Next, processing contents of the information processing apparatus 100 will be explained by using FIGS. 4 to 27. The vector display processing unit 120 performs a display to prompt the user to select a display target on the display unit 150, and input unit 140 accepts selection of the display target from the user (FIG. 4: step S1). In this embodiment, it is presumed that either of the right ventricle and left ventricle is selected. The input unit 140 outputs data of the selected display target to the vector display processing unit 120. The vector display processing unit 120 accepts the data of the selected display target from the input unit 140.

Figure 5:
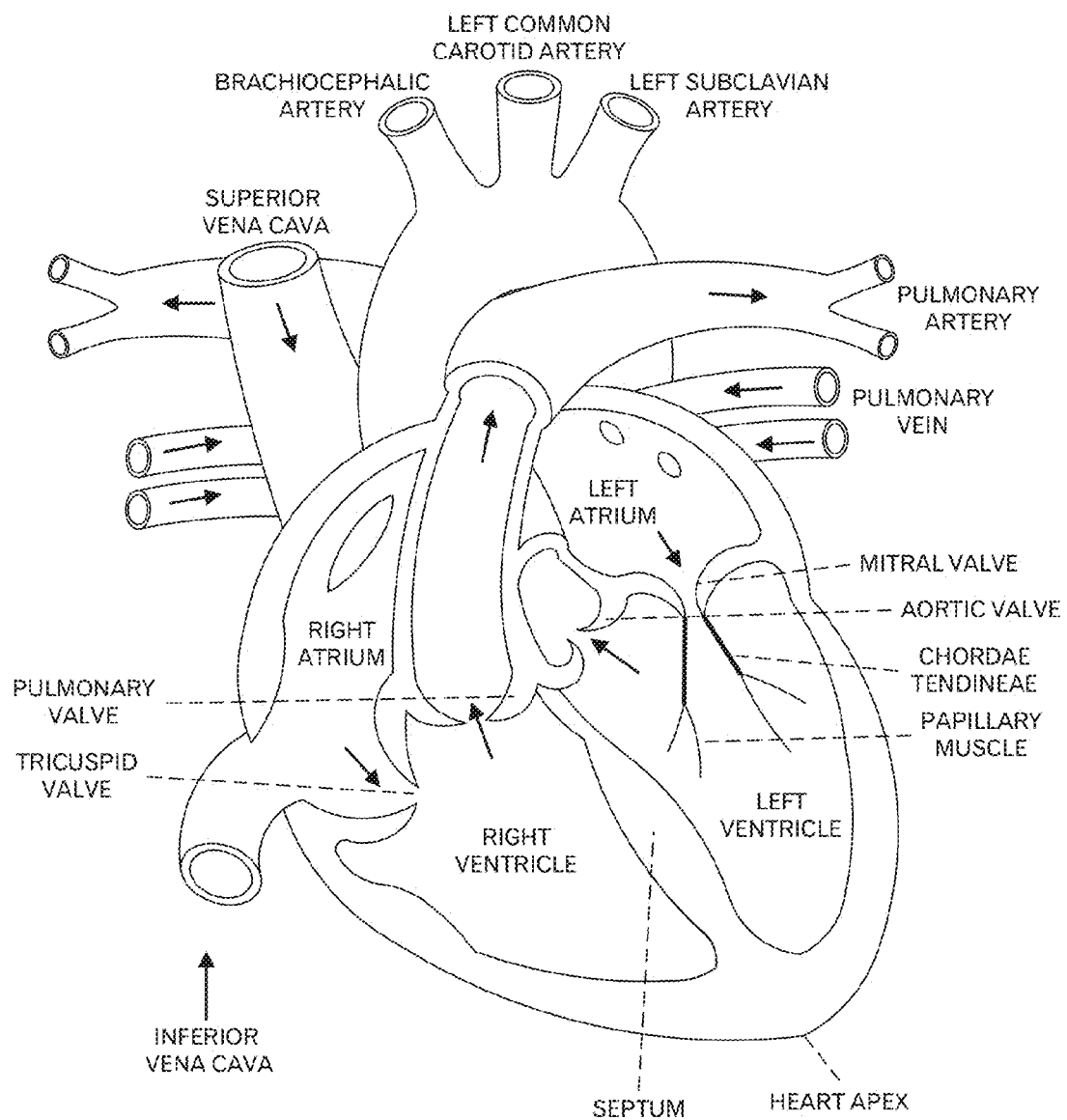
FIG. 5 is a schematic diagram depicting a structure of a heart.

The structure of the heart is as illustrated in FIG. 5, for example. The blood flows into the right ventricle from the tricuspid valve, and the blood flows out from the right ventricle through the pulmonary valve. Moreover, the blood flows into the left ventricle from the mitral valve, and the blood flows out from the left ventricle through the aortic valve. The apex portion is identified as a reference point in a lower portion of the heart. In addition to the apex portion, an apex portion of the right ventricle is also identified in the bottom inside of the right ventricle.

Then, the axis processing unit 121 calculates preset axis candidates for the selected display target, and stores data of the axis candidates in the second data storage unit 130 (step S3).

In this embodiment, when the left ventricle is selected as a display target, three axis candidates are calculated. However, the axis candidates may be set manually in advance, and stored in the second data storage unit 130 or the like.

Figure 6:
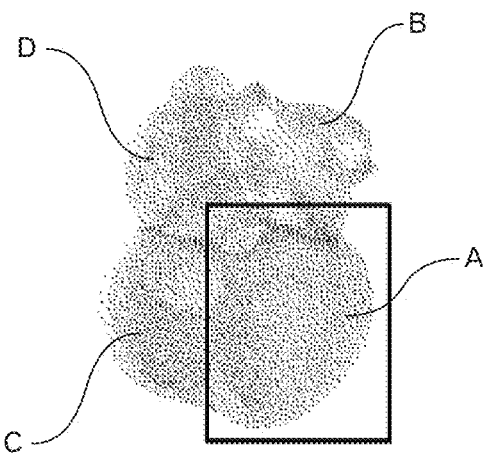
FIG. 6 is a diagram depicting an entire heart.
Figure 7:
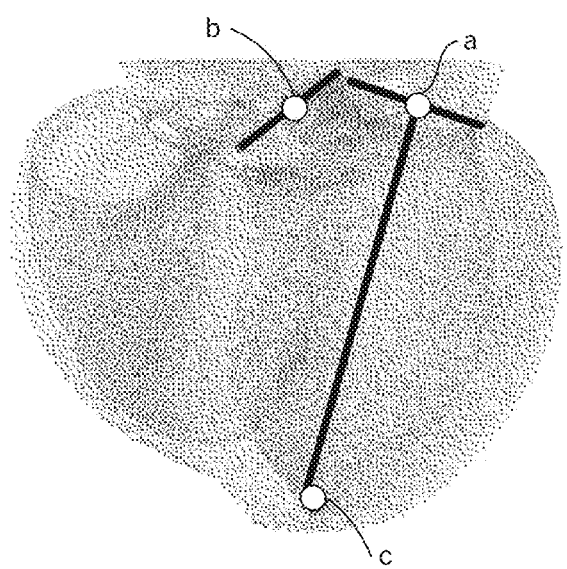
FIG. 7 is a diagram depicting an example of a first axis candidate identified in the left ventricle.

For example, the heart as illustrated in FIG. 6 has the left ventricle A, left atrium B, right ventricle C and right atrium D, and when paying attention to the left ventricle A, a line segment connecting a center a of gravity for a surface region including an annulus of the mitral valve with the apex portion c as a first axis candidate is calculated as illustrated in FIG. 7. The surface region including the annulus of the mitral valve or the center a of gravity for the surface region including the annulus of the mitral valve may be preset, or may be extracted from its features. The apex portion c may be preset or may be extracted from its features.

Figure 8:
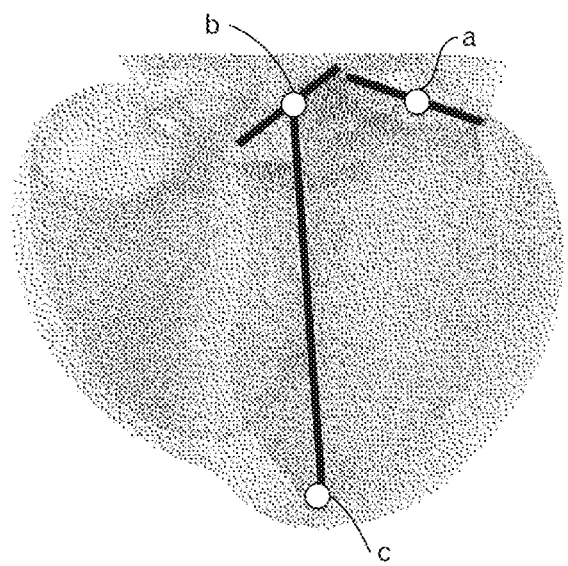
FIG. 8 is a diagram depicting an example of a second axis candidate identified in the left ventricle.

In addition, as illustrated in FIG. 8, a line segment connecting a center b of gravity for a surface region including the annulus of the aortic valve with the apex portion c is calculated as the second axis candidate. The annulus of the aortic valve or the center b of gravity for the surface region including the annulus of the aortic valve may be preset or may be extracted from its features.

Figure 9:
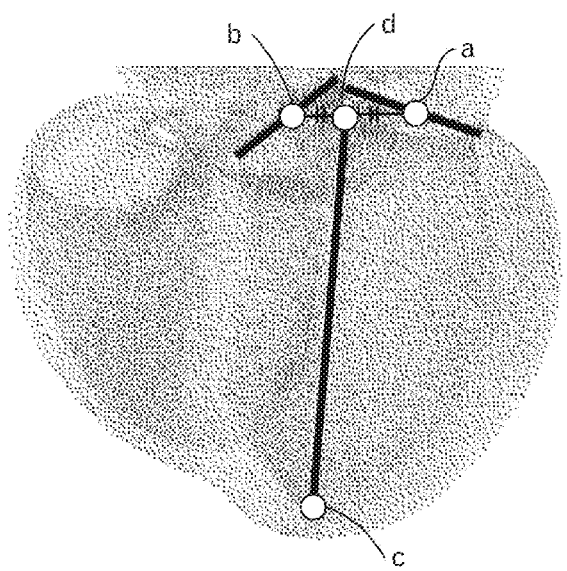
FIG. 9 is a diagram depicting an example of a third axis candidate identified in the left ventricle.

Furthermore, as illustrated in FIG. 9, a line segment connecting a middle point d between the center a of gravity for the surface region including the annulus of the mitral valve and the center b of gravity for the surface region including the annulus of the aortic valve with the apex portion c is calculated as the third axis candidate.

Moreover, when the right ventricle C is selected as the display target, four axis candidates are calculated. However, the axis candidates may be preset manually, and stored in the second data storage unit 130 or the like.

Figure 10:
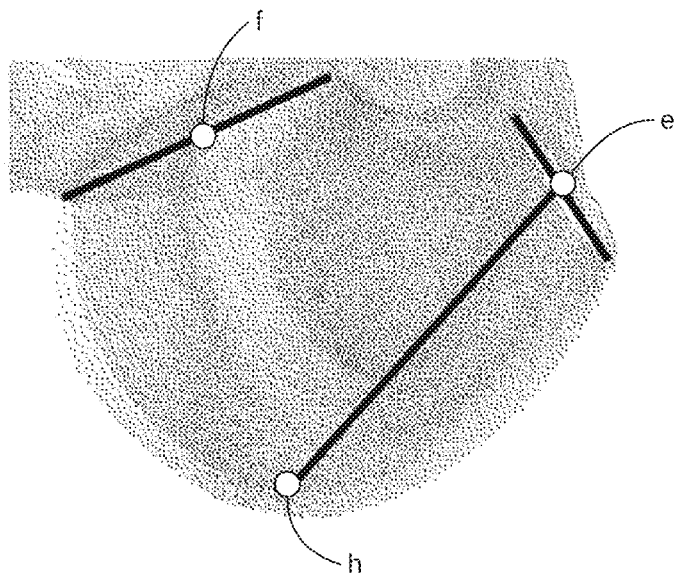
FIG. 10 is a diagram depicting an example of a first axis candidate identified in the right ventricle.

For example, as illustrated in FIG. 10, a line segment connecting a center e of gravity for a surface region including an annulus of the pulmonary valve with an apex portion h of the right ventricle is calculated as the first axis candidate. The annulus of the pulmonary valve or the center e of gravity for the surface region including the annulus of the pulmonary valve may be preset, or may be extracted from its features. The apex portion h of the right ventricle is a bottom portion of the right ventricle furthest from the center e of gravity for the surface region including the annulus of the pulmonary and a center f of gravity for the surface region including the annulus of the tricuspid valve, and may be extracted from its features, or may be preset.

Figure 11:
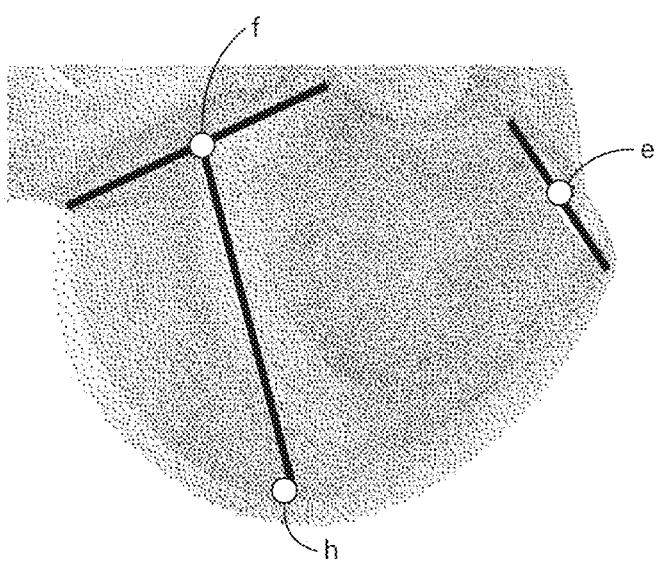
FIG. 11 is a diagram depicting an example of a second axis candidate identified in the right ventricle.

Moreover, as illustrated in FIG. 11, a line segment connecting the center f of gravity for the surface region including the annulus of the tricuspid valve with the apex portion h of the right ventricle is calculated as the second axis candidate. The annulus of the tricuspid valve or the center f of gravity for the surface region including the annulus of the tricuspid valve may be preset, or may be extracted from its features.

Figure 12:
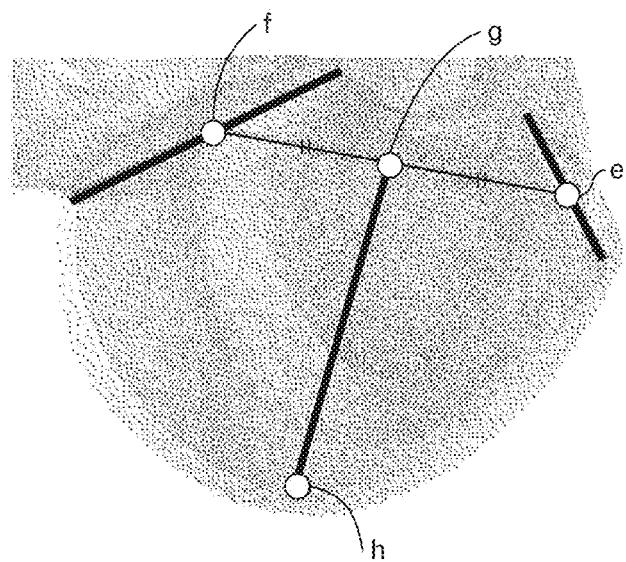
FIG. 12 is a diagram depicting an example of a third axis candidate identified in the right ventricle.

Furthermore, as illustrated in FIG. 12, a line segment connecting a middle point g between the center f of gravity for the surface region including the annulus of the tricuspid valve and the center e of gravity for the surface region including the annulus of the pulmonary valve with the apex portion h of the right ventricle is calculated as the third candidate.

Figure 13:
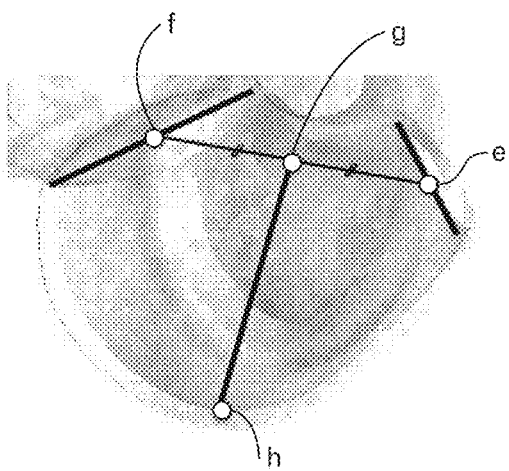
FIG. 13 is a diagram to explain a process to calculate a fourth axis candidate identified in the right ventricle.
Figure 14:
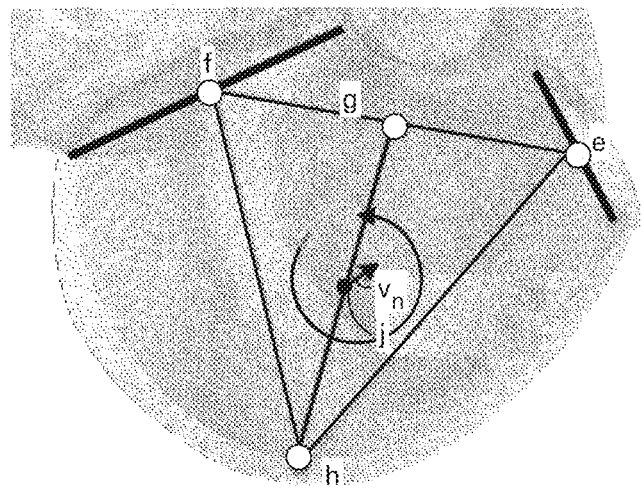
FIG. 14 is a diagram to explain the process to calculate the fourth axis candidate identified in the right ventricle.
Figure 15:
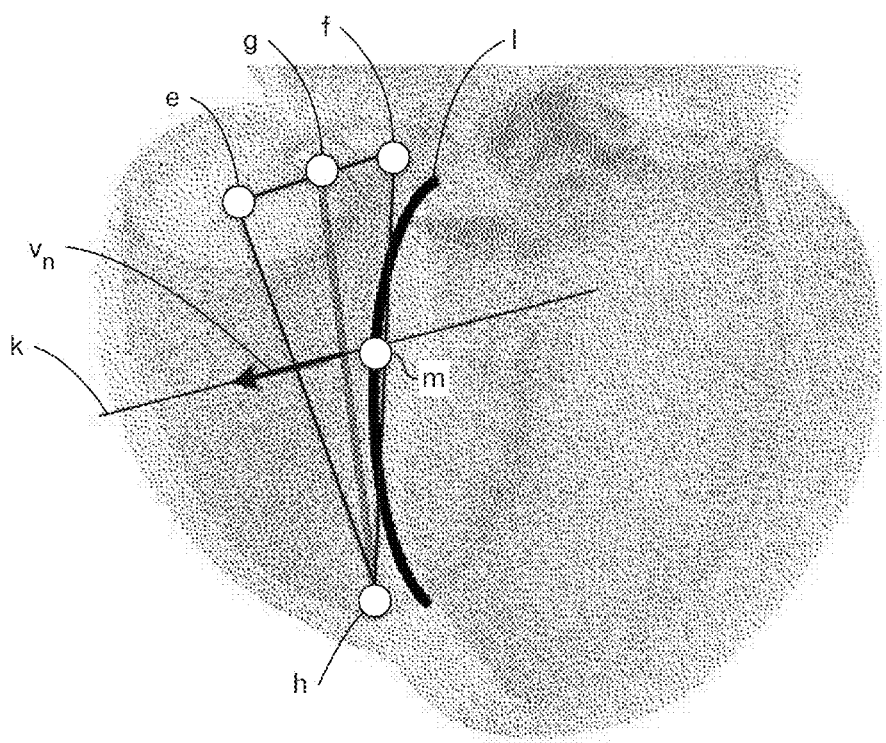
FIG. 15 is a diagram to explain the process to calculate the fourth axis candidate identified in the right ventricle.
Figure 16:
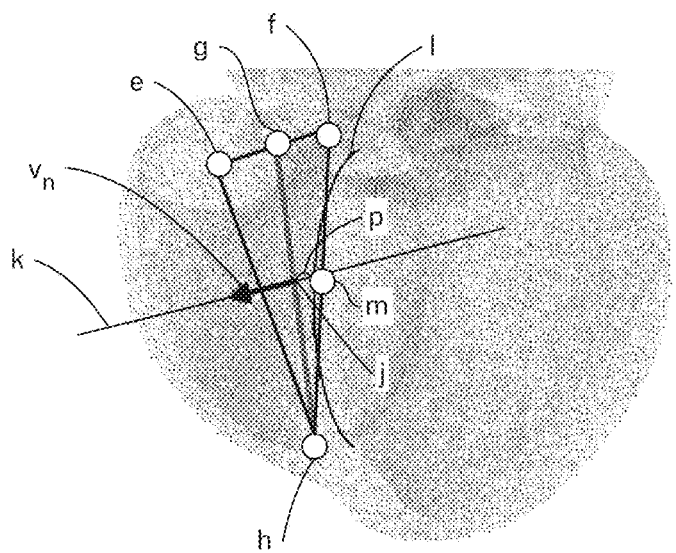
FIG. 16 is a diagram to explain the process to calculate the fourth axis candidate identified in the right ventricle.
Figure 17:
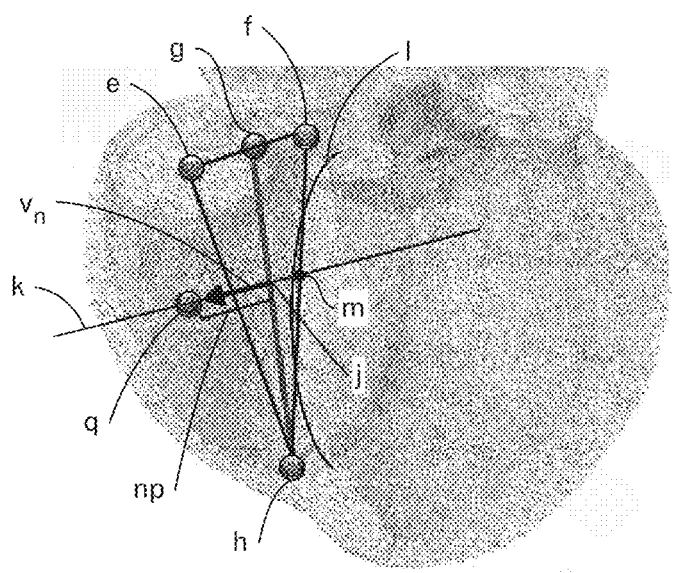
FIG. 17 is a diagram to explain the process to calculate the fourth axis candidate identified in the right ventricle.
Figure 18:
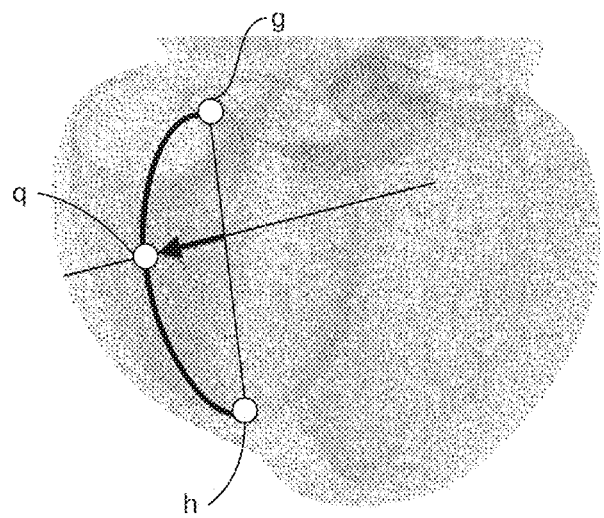
FIG. 18 is a diagram to explain the process to calculate the fourth axis candidate identified in the right ventricle.

Moreover, because the right ventricle has an arch form, and an axis of a curved line along the arch form may be adopted. In such a case, as illustrated in FIG. 13, a line segment connecting a middle point g between the center f of gravity for the surface region including the annulus of the tricuspid valve and the center e of gravity for the surface region including the annulus of the pulmonary valve with the apex portion h of the right ventricle is generated, and as illustrated in FIG. 14, at a middle point j of this line segment, a normal vector $v_n$ having a direction that follows the corkscrew rule in order of the points e, f and h is generated. Furthermore, as illustrated in FIG. 15, a straight line k passing through the normal vector $v_n$ is traced to identify a point m on a boundary surface l (i.e. a fluid surface of the heart muscle) that is nearest to the middle point j. Then, as illustrated in FIG. 16, a distance p between the points j and m is calculated, and as illustrated in FIG. 17, a point q is identified, which is far away from the point j on the straight line k by a predetermined number n (n is equal to or greater than 2)*p. Finally, as illustrated in FIG. 18, a curved line smoothly connecting the points g, h and q (e.g. by a spline curve) is calculated as the axis fourth candidate.

Then, the axis processing unit 121 outputs the axis candidates onto the display unit 150 to prompt the user to select an axis to be employed (step S5). The input unit 140 accepts a selection instruction of the axis from the user (step S7), and outputs data of the selected axis to the vector display processing unit 120. The vector display processing unit 120 receives the data of the selected axis from the input unit 140.

Next, the plane generator 122 prompts the user to designate the number of cross sections and a resolution of the surface region, and the input unit 140 accepts the designation of the number of cross sections and the resolution of the surface region, and outputs data of the number of cross sections and the resolution of the surface region to the plane generator 122 (step S9). The plane generator 122 receives the data of the number of cross sections and the resolution of the surface region from the input unit 140.

Then, the plane generator 122 generates Z surface regions (Z=the number of cross sections) having the designated resolution and being orthogonal to the axis designated at the step S7, and stores data of the generated surface regions into the second data storage unit 130 (step S11).

Figure 19:
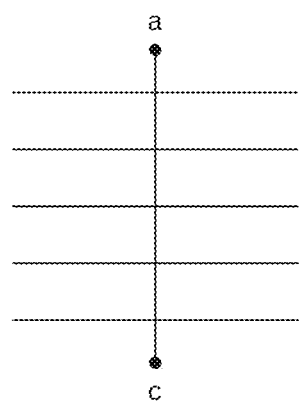
FIG. 19 is a diagram to explain a position of a surface region.
Figure 20:
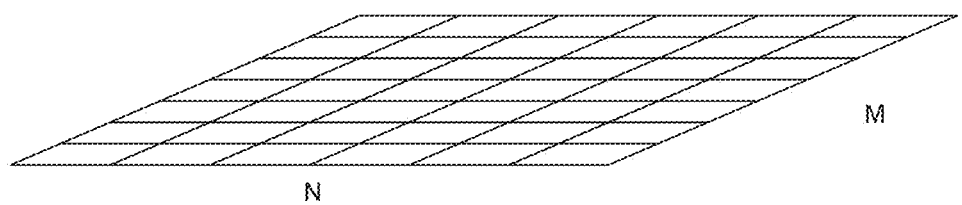
FIG. 20 is a diagram to explain lattice points on the surface region.

For example, when the line segment connecting the center a of gravity for the surface region including the annulus of the mitral valve with the apex portion c is designated and the number of cross sections is "5" as illustrated in FIG. 19, 5 surface regions are generated that has a predetermined size and whose center position is at a position obtained by equally dividing the line segment ac by "6". Furthermore, as illustrated in FIG. 20, N*M lattice points (or grid points) (M is designated as the resolution.) are defined on the surface region.

Then, the vector generator 123 calculates, for each surface region, a vector at each lattice point in the surface region from the vectors at vertexes of the unstructured grid (tetrahedral elements in this embodiment), and stores calculation results into the second data storage unit 130 (step S13).

Figure 21:
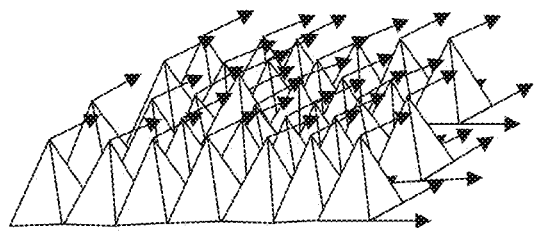
FIG. 21 is a diagram to explain a processing for calculating vectors at the lattice points.

In this embodiment, as illustrated in FIG. 21, a vector at each vertex of the tetrahedral elements is defined in the first data storage unit 110 for a portion that is other than the heart muscle and in which the blood flows. Therefore, for each lattice point, a tetrahedral element encompassing this lattice point is identified to calculate a vector at the lattice point from the vector at each vertex of the tetrahedral element.

Figure 22:
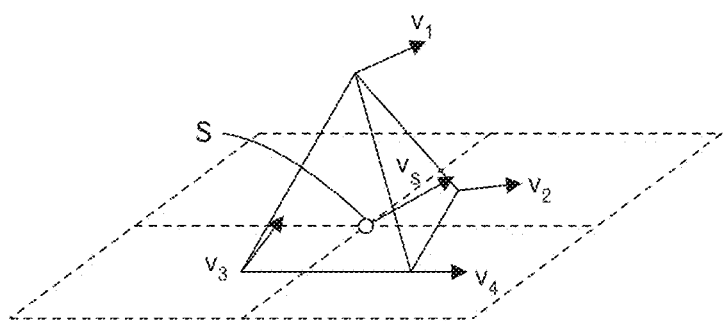
FIG. 22 is a diagram to explain the processing for calculating vectors at the lattice points.

In other words, as illustrated in FIG. 22, a lattice point s is included in the depicted tetrahedral element. Vectors $v_1$ to $v_4$ are defined at vertexes of this tetrahedral element. Therefore, the vector $v_s$ at the lattice point s is calculated as follows:

$$v_s = \frac{\sum_{i}^{4} v_i N_i}{\sum_{i}^{4} N_i}$$

$$N_i = \frac{1}{d_i}$$

"$d_i$" represents a distance between the lattice point s included in the tetrahedral element and each vertex position i of the tetrahedral element. Thus, the vector $v_s$ at the lattice point s is a vector obtained by linearly interpolating the vectors $v_1$ to $v_4$ at the respective vertexes.

Moreover, the vector generator 123 sets a magnitude of the vector by multiplying a magnification, which is initially set, by magnitude of the calculated vector (step S15).

Figure 23:
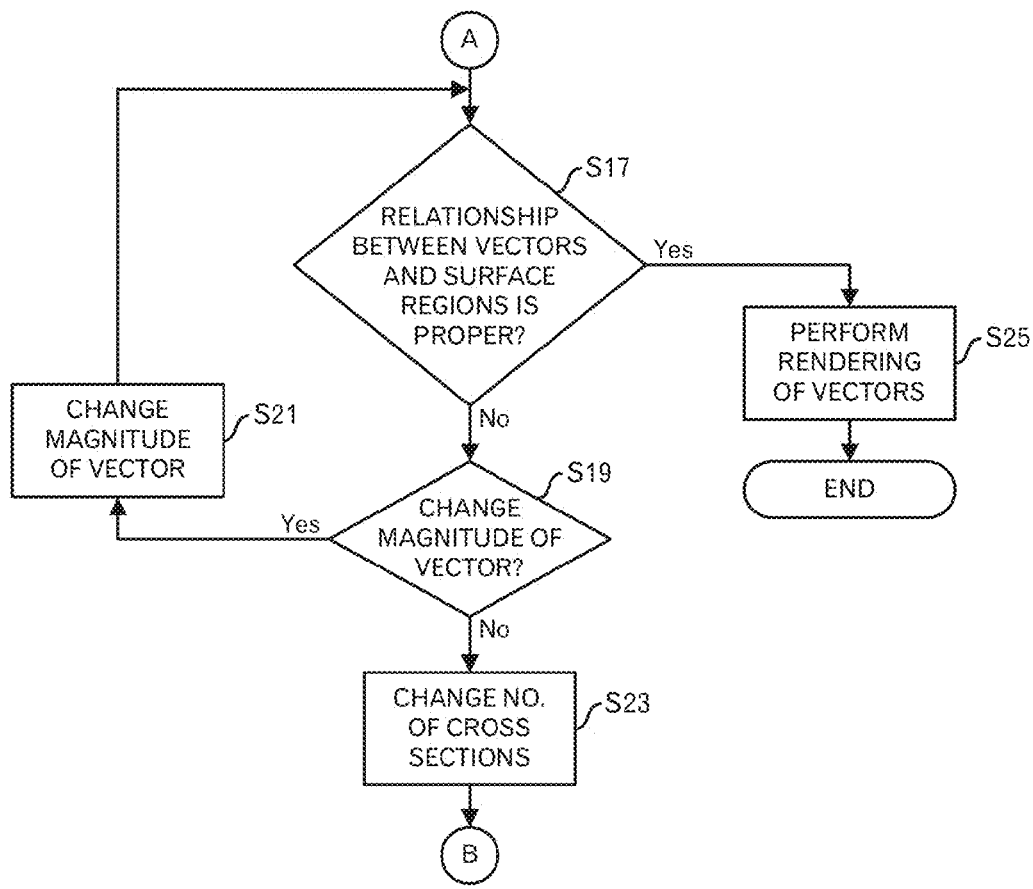
FIG. 23 is a diagram depicting a processing flow relating to this embodiment.

Shifting to the processing of FIG. 23, the vector display processing unit 120 determines whether or not a relationship between the vector and the surface region is appropriate (step S17). For example, when the vector is tangent to or penetrates a surface region different from the surface region of a start point of the vector, it is determined that the relationship between the vector and the surface region is not appropriate. Therefore, it is determined, for each surface region, whether or the vector at each lattice point satisfies such a condition.

When the relationship between the vector and the surface region is appropriate, the rendering processing unit 124 performs rendering by using data stored in the first data storage unit 110 for the portions other than the heart muscle, using vector data stored in the second data storage unit 130 for the portions in which the blood flows, and displaying the vectors as the arrows (step S25). Then, the processing ends. As described above, when the processing is performed for plural time steps, the processing shifts to a processing for the next step. In the processing for the next step, the number of cross sections and resolution may not be changed.

On the other hand, when the relationship between the vector and the surface region is not appropriate, the vector display processing unit 120 prompts the user to input whether or not the magnitude of the vector is changed, and the input unit 140 accepts an input concerning whether or not the magnitude of the vector is changed. Then, when the magnitude of the vector is changed (step S19: Yes route), the vector generator 123 changes the magnitude of the vector (step S21). For example, when the magnitude of the vector may be changed by multiplying the present magnitude of the vector by a predetermined reduction ratio that is less than "1", the predetermined ratio may be designated again by the user. Then, the processing returns to the step S17.

On the other hand, when the magnitude of the vector is not changed (step S19: No route), the number of cross sections is changed. Therefore, the plane generator 122 performs display on the display unit 150 to prompt the user to change the number of cross sections, and the input unit 140 accepts an input of the changed number of cross sections from the user (step S23). Then, the input unit 140 outputs data of the changed number of cross sections to the plane generator 122. Then, the processing returns to the step S11 through terminal B.

By carrying out such a processing, the arrow corresponding to the vector can be displayed at appropriate intervals.

Figure 1:
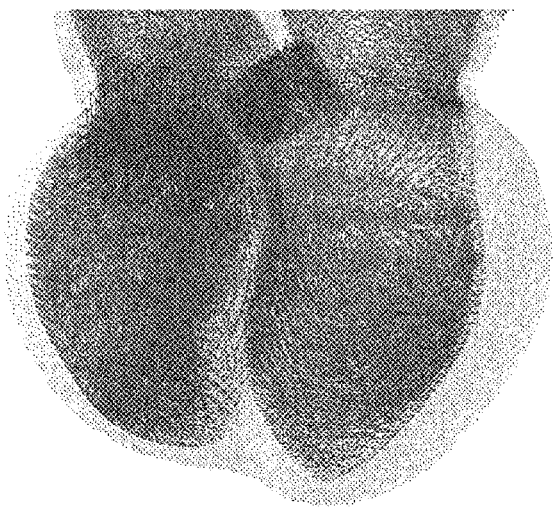
FIG. 1 is a diagram to explain a problem of a conventional art.
Figure 2:
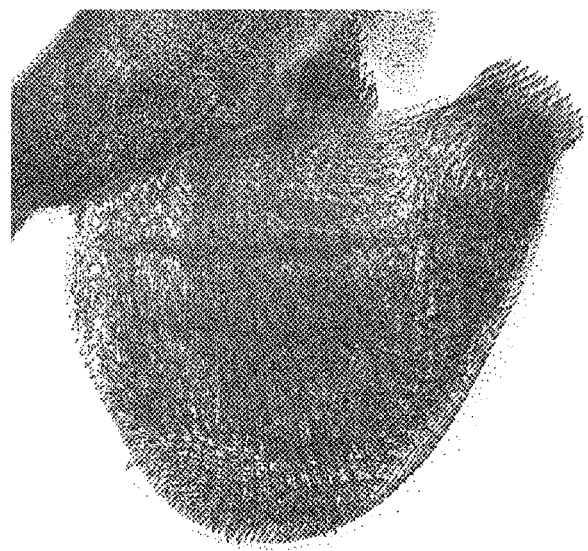
FIG. 2 is a diagram to explain the problem of the conventional art.
Figure 24:
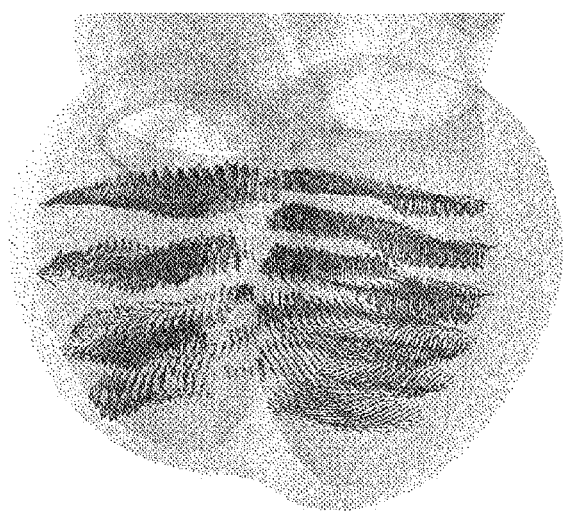
FIG. 24 is a diagram to explain an effect of this embodiment.
Figure 25:
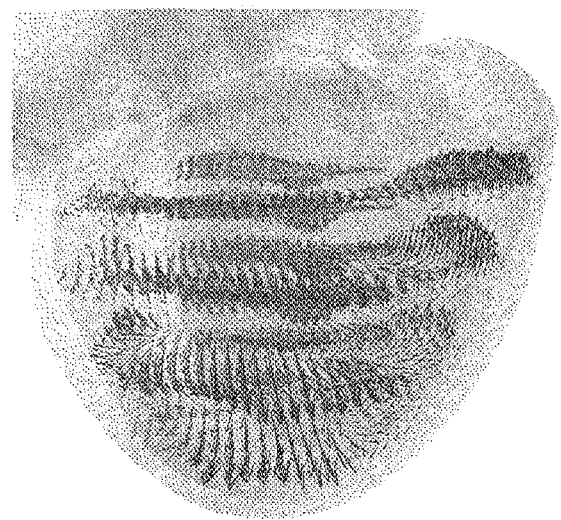
FIG. 25 is a diagram depicting an effect of this embodiment.

For example, when a processing result of this embodiment is illustrated at the same angle as in FIG. 1, a state as illustrated in FIG. 24 is obtained. According to this figure, it becomes easy to understand how the blood flows. Similarly, when a processing result of this embodiment is illustrated at the same angle as in FIG. 2, a state as illustrated in FIG. 25 is obtained. Also according to this figure, it becomes possible to understand how the blood flows.

Figure 26:
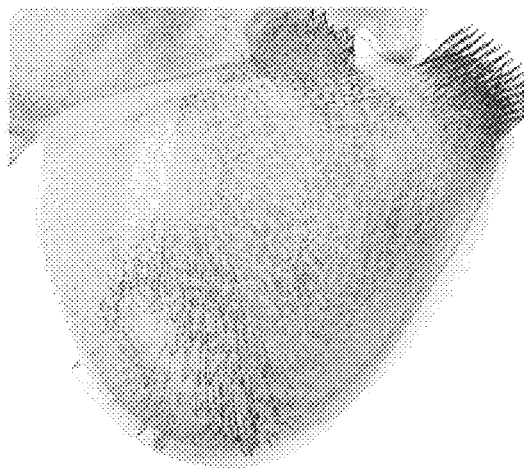
FIG. 26 is a diagram depicting an example in which the right ventricle is displayed by the conventional art.
Figure 27:
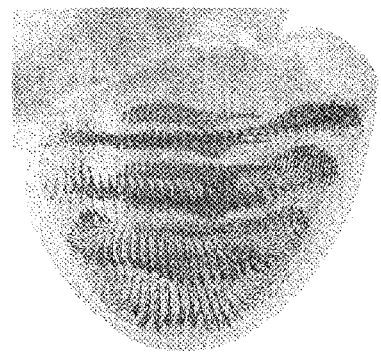
FIG. 27 is a diagram depicting an example in which the right ventricle is displayed by this embodiment.

Furthermore, when the right ventricle is selected, a display as illustrated in FIG. 26 is made in the conventional art. However, when this embodiment is carried out as selecting the curved axis as the axis, a display as illustrated in FIG. 27 is performed. In FIG. 26, the arrows are tangled, and it is difficult to understand the blood flow. However, in an example of FIG. 27, it becomes possible to roughly understand the blood flow.

Although the embodiments of this invention are described, this invention is not limited to the embodiments. For example, the functional block diagram illustrated in FIG. 3 is a mere example, and does not always correspond to a program module configuration. Furthermore, as for the processing flow, various changes can be made. For example, as long as the processing results do not change, an order of steps may be changed, and plural steps may be executed in parallel. Furthermore, a processing for identifying an axis may be performed by various methods. In the aforementioned example, an example in which an axis is designated after the display target is designated was explained. However, without designating the display target, axis candidates may be presented, or after performing a display once according to an axis that is initially set, the axis may be changed according to the user's designation.

Furthermore, the aforementioned processing may be executed by one computer or by plural computers in parallel.

Figure 28:
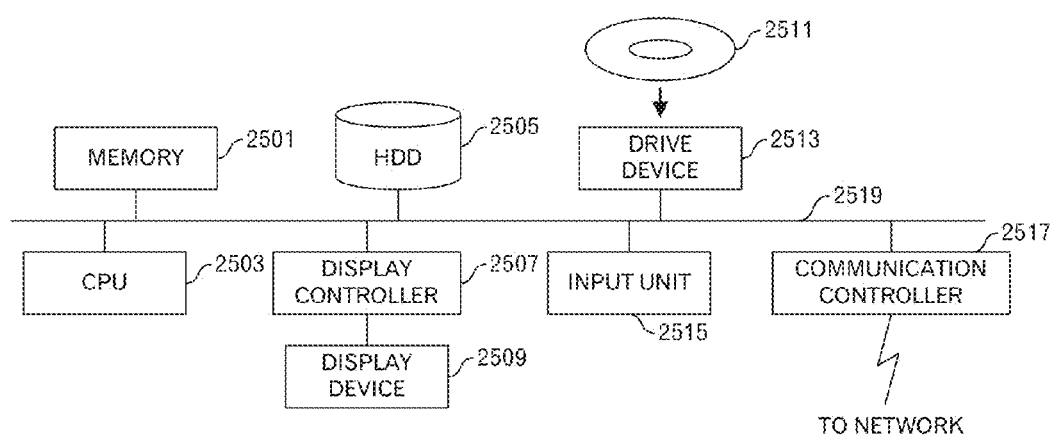
FIG. 28 is a functional block diagram of a computer.

In addition, the aforementioned information processing apparatus 100 is a computer devices as illustrated in FIG. 28. That is, a memory 2501 (storage device), a CPU 2503 (processor), a hard disk drive (HDD) 2505, a display controller 2507 connected to a display device 2509, a drive device 2513 for a removable disk 2511, an input device 2515, and a communication controller 2517 for connection with a network are connected through a bus 2519 as illustrated in FIG. 28. An operating system (OS) and an application program for carrying out the foregoing processing in the embodiment, are stored in the HDD 2505, and when executed by the CPU 2503, they are read out from the HDD 2505 to the memory 2501. As the need arises, the CPU 2503 controls the display controller 2507, the communication controller 2517, and the drive device 2513, and causes them to perform predetermined operations. Moreover, intermediate processing data is stored in the memory 2501, and if necessary, it is stored in the HDD 2505. In this embodiment of this technique, the application program to realize the aforementioned functions is stored in the computer-readable, non-transitory removable disk 2511 and distributed, and then it is installed into the HDD 2505 from the drive device 2513. It may be installed into the HDD 2505 via the network such as the Internet and the communication controller 2517. In the computer as stated above, the hardware such as the CPU 2503 and the memory 2501, the OS and the application programs systematically cooperate with each other, so that various functions as described above in details are realized.

The aforementioned embodiments are outlined as follows:

A display processing method relating to the embodiments includes: (A) identifying an axis that is a straight or curved line inside of a space; (B) first generating plural surface regions that are orthogonal to the identified axis; (C) second generating, from a first vector provided at each vertex of an unstructured grid disposed inside of the space, a second vector at each point of plural points on a surface region for each of the generated plural surface regions, wherein the first vectors are stored in a data storage unit; and (D) displaying an arrow corresponding to the generated second vector.

By carrying out such a processing, vectors are represented as arrows, which are dispersed appropriately on plural surface regions that are disposed appropriately, instead of displaying an unclear state in which the arrows are tangled in the space. Therefore, it becomes possible to easily confirm the state of the fluid inside of the space.

Moreover, the aforementioned display processing method may further include: (E) determining whether or not a certain arrow corresponding to the generated second vector intersects with another surface region or a tip of the certain arrow corresponding to the generated second vector is tangent to the another surface region; (F) upon determining that the certain arrow corresponding to the generated second vector intersects with the another surface region or the tip of the certain arrow corresponding to the generated second vector is tangent to the another surface region, generating plural second surface regions that are orthogonal to the identified axis; and (G) generating, from the first vector, a second vector at each point of plural points on each second surface region for each of the generated plural second surface regions.

According to this configuration, it is possible to adjust the positions of the surface regions so as to enable the user to easily see the arrows corresponding to the vectors.

On the other hand, the aforementioned display processing method may further include: (H) determining whether or not a certain arrow corresponding to the generated second vector intersects with another surface region or a tip of the certain arrow corresponding to the generated second vector is tangent to the another surface region; and (I) upon determining that the certain arrow corresponding to the generated second vector intersects with the another surface region or the tip of the certain arrow corresponding to the generated second vector is tangent to the another surface region, changing magnitude of the generated second vector.

In order to enable the user to easily see the arrows corresponding to the vectors, the length of the arrow is shortened.

Moreover, the aforementioned identifying may include: identifying one of at least a line segment connecting a first center of gravity for a surface region including a mitral valve (in detail, annulus thereof) of a heart with an apex of the heart, a line segment connecting a second center of gravity for a surface region including an aortic valve (in detail, annulus thereof) with the apex of the heart, a line segment connecting a first middle point between the first center of gravity and the second center of gravity with the apex of the heart, a line segment connecting a third center of gravity for a surface region including a pulmonary valve (in detail, annulus thereof) of the heart with an apex portion of a right ventricle in the heart, a line segment connecting a fourth center of gravity for a surface region including a tricuspid valve (in detail, annulus thereof) with the apex portion of the right ventricle, a line segment connecting a second middle point between the third center of gravity and the fourth center of gravity with the apex portion of the right ventricle, and a curved line connecting the second middle point with the apex portion of the right ventricle.

When the blood flow in the right ventricle or left ventricle of the heart is displayed, any of these axes is preferable.

Furthermore, the aforementioned first generating may include: generating the plural surface regions at positions obtained by equally dividing the identified axis based on a designated number (in detail, by the designated number+1). Thus, it is possible to easily see the vectors.

Incidentally, it is possible to create a program causing a computer to execute the aforementioned processing, and such a program is stored in a computer readable storage medium or storage device such as a flexible disk, CD-ROM, DVD-ROM, magneto-optic disk, a semiconductor memory, and hard disk. In addition, the intermediate processing result is temporarily stored in a storage device such as a main memory or the like.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present inventions have been described in detail, it should be understood that the various changes, substitutions, and alterations could be made hereto without departing from the spirit and scope of the invention.

What is claimed is:

1. A computer-readable, non-transitory storage medium storing a program for causing a computer to execute a process, the process comprising:

identifying an axis that is a straight or curved line inside of a space;

first generating plural surface regions that are orthogonal to the identified axis;

second generating, for each of plural unstructured grids disposed inside the space, a first vector at a point, based on a second vector at each vertex of the unstructured grid, wherein the point is included in the unstructured grid and is located on one of the plural surface regions;

determining whether or not a certain arrow corresponding to the generated first vector intersects with another surface region or a tip of the certain arrow corresponding to the generated first vector is tangent to the another surface region;

upon determining that the certain arrow corresponding to the generated first vector intersects with the another surface region or the tip of the certain arrow corresponding to the generated first vector is tangent to the another surface region, third generating plural second surface regions that are orthogonal to the identified axis;

fourth generating, for each of the plural unstructured grid disposed inside the space, a third vector at a point, based on the second vector at each vertex of the unstructured grid, wherein the point is included in the unstructured grid and is located on one of the plural second surface regions; and displaying an arrow corresponding to the generated third vector.

2. The computer-readable, non-transitory storage medium as set forth in claim 1, wherein the process further comprises:

determining whether or not a certain arrow corresponding to the generated third vector intersects with another surface region or a tip of the certain arrow corresponding to the generated third vector is tangent to the another surface region; and upon determining that the certain arrow corresponding to the generated third vector intersects with the another surface region or the tip of the certain arrow corresponding to the generated third vector is tangent to the another surface region, changing magnitude of the generated third vector.

3. The computer-readable, non-transitory storage medium as set forth in claim 1, wherein the identifying comprises:

identifying one of at least a line segment connecting a first center of gravity for a surface region including a mitral valve of a heart with an apex of the heart, a line segment connecting a second center of gravity for a surface region including an aortic valve with the apex of the heart, a line segment connecting a first middle point between the first center of gravity and the second center of gravity with the apex of the heart, a line segment connecting a third center of gravity for a surface region including a pulmonary valve of the heart with an apex portion of a right ventricle in the heart, a line segment connecting a fourth center of gravity for a surface region including a tricuspid valve with the apex portion of the right ventricle, a line segment connecting a second middle point between the third center of gravity and the fourth center of gravity with the apex portion of the right ventricle, and a curved line connecting the second middle point with the apex portion of the right ventricle.

4. The computer-readable, non-transitory storage medium as set forth in claim 1, wherein the first generating comprises:

generating the plural surface regions at positions obtained by equally dividing the identified axis based on a designated number.

5. A display processing method, comprising:

identifying, by using a computer, an axis that is a straight or curved line inside of a space;

first generating, by using the computer, plural surface regions that are orthogonal to the identified axis;

second generating, by using the computer, for each of plural unstructured grids disposed inside the space, a first vector at a point, based on a second vector at each vertex of the unstructured grid, wherein the point is included in the unstructured grid and is located on one of the plural surface regions;

determining, by using the computer, whether or not a certain arrow corresponding to the generated first vector intersects with another surface region or a tip of the certain arrow corresponding to the generated first vector is tangent to the another surface region;

upon determining that the certain arrow corresponding to the generated first vector intersects with the another surface region or the tip of the certain arrow corresponding to the generated first vector is tangent to the another surface region, third generating, by using the computer, plural second surface regions that are orthogonal to the identified axis;

fourth generating, by using the computer and for each of the plural unstructured grid disposed inside the space, a third vector at a point, based on the second vector at each vertex of the unstructured grid, wherein the point is included in the unstructured grid and is located on one of the plural second surface regions; and displaying, by using the computer, an arrow corresponding to the generated third vector.

6. A display processing apparatus, comprising:

a memory; and a processor configured to use the memory and execute a process, the process comprising:

identifying an axis that is a straight or curved line inside of a space;

first generating plural surface regions that are orthogonal to the identified axis;

second generating, for each of plural unstructured grids disposed inside the space, a first vector at a point, based on a second vector at each vertex of the unstructured grid, wherein the point is included in the unstructured grid and is located on one of the plural surface regions;

determining whether or not a certain arrow corresponding to the generated first vector intersects with another surface region or a tip of the certain arrow corresponding to the generated first vector is tangent to the another surface region;

upon determining that the certain arrow corresponding to the generated first vector intersects with the another surface region or the tip of the certain arrow corresponding to the generated first vector is tangent to the another surface region, third generating plural second surface regions that are orthogonal to the identified axis;

fourth generating, for each of the plural unstructured grid disposed inside the space, a third vector at a point, based on the second vector at each vertex of the unstructured grid, wherein the point is included in the unstructured grid and is located on one of the plural second surface regions; and displaying an arrow corresponding to the generated third vector.

* * * * *